United States Patent [19]

Nappin

[11] 4,145,741
[45] Mar. 20, 1979

[54] SIGNAL PROCESSING ARRANGEMENTS

[76] Inventor: Donald Nappin, South Harrow, England

[21] Appl. No.: 816,946

[22] Filed: Jul. 19, 1977

[30] Foreign Application Priority Data

Jul. 23, 1976 [GB] United Kingdom ............... 30764/76

[51] Int. Cl.² .............................................. G06G 7/12
[52] U.S. Cl. .................................... 364/571; 364/516; 364/415
[58] Field of Search ............... 364/516, 517, 571, 722, 364/487, 415; 340/16 R, 15.5 DP; 343/5 R, 5 DP

[56] References Cited

U.S. PATENT DOCUMENTS

| 3,407,355 | 10/1968 | Clark et al. ...................... 364/517 X |
| 3,504,164 | 3/1970 | Farrell et al. ......................... 364/487 |
| 3,832,537 | 8/1974 | Marutani .............................. 364/517 |
| 4,038,530 | 7/1977 | Miyahara et al. .................... 364/516 |

Primary Examiner—Edward J. Wise
Attorney, Agent, or Firm—Fleit & Jacobson

[57] ABSTRACT

For systems, such as ultrasonic investigative systems, analyzing pulses received after transmission or reflection, it is known to apply swept gain to the received signal to overcome loss in propagation. This is achieved in this invention by converting the signals to log form and subtracting the log of the loss function. The signals may then be antilog converted. The subtraction can be by passing only signals above a threshold set at the figure to be subtracted.

6 Claims, 6 Drawing Figures

SIGNAL PROCESSING ARRANGEMENTS

The present invention relates to processing signals representative of received pulses of energy which have been subject to attenuation during propagation.

Systems, such as radar or ultrasonic investigative systems, using reflection of transmitted pulses to determine the position of an object or other reflective feature, generally process the signals in terms of elapsed time between emission of a pulse and reception of a reflected pulse. However the amplitude of the received pulses decreases with increasing distance of the cause of reflection. For radar arrangements attenuation (loss) depends on the fourth power of distance since the medium of propagation is effectively lossless. However for ultrasonic systems the attenuation law depends on the actual medium, the frequency of the pulses and factors of system geometry. Typically, for an ultrasonic system examining a body tissue, losses approximate an exponential value with distance of 2dB/cm, for a single transit at 2MHz as indicated in FIG. 1.

For such systems a swept gain amplifier may be used to provide time-varied-gain (T.V.G.). In ultrasonic applications this is implemented by sweeping the amplifier gain as a function of time, and therefore of range, assuming the medium to be uniform. Typically such an amplifier might comprise stages of gain, perhaps using dual gate field effect transistors, with a ramp voltage applied to one gate and the signal to the other.

The effect achieved is that of dividing the received signal by the loss function of the medium through which the signal has been propagated. However in practice the required function can be difficult to set up and to maintain and difficult to change, to provide functions for different media.

In certain circumstances it is desirable to convert the received signals into logarithmic forms and in those circumstances it has been suggested that the signal be subject to time varied gain prior to log amplification so as to restrict the signals to the dynamic range of the amplifier (IEEE transactions on sonics and ultrasonics vol. 11–12 1965 pp. 31–37.

It is an object of this invention to provide an alternative arrangement especially, though not exclusively, suitable for ultrasonic use.

According to the present invention there is provided an arrangement for processing signals, representing received pulses of energy which have been subject to attenuation which is a function of their propagation time, including means for converting the signals to logarithmic form and means for effectively subtracting therefrom a further signal, representing the logarithm of the attenuation function, to make the signals more representative of said pulses in the absence of attenuation.

In order that the invention may be clearly understood and readily carried into effect an example thereof will now be described with reference to the accompanying drawings, of which:

FIG. 1 has the significance described hereinbefore,

To provide the required swept gain the incoming signal, which is the product of the desired echo signal E and a loss function L, is subject to logarithmic conversion in a logarithmic amplifier to provide Log LE and a signal of log L is subtracted therefrom to give Log LE − Log L = Log E, which may be required or which may be converted to give E.

It should be understood that, although the loss function L is unipolar, the desired echo signal E is bipolar so that a practical circuit cannot straightforwardly implement the above equations.

The arrangement of this invention uses a practical 'logarithmic' amplifier having an instantaneous output which is in effect the logarithm of the modulus of the instantaneous input and has the same sign as that input. Furthermore the practical amplifier avoids the low input region, for which, strictly, the logarithm should tend to $-\infty$, by having an approximately linear transfer around the origin and only being logarithmic above a predetermined level. In this specification a 'logarithmic' amplifier is to be understood to be such a practical amplifier.

Figure 2:
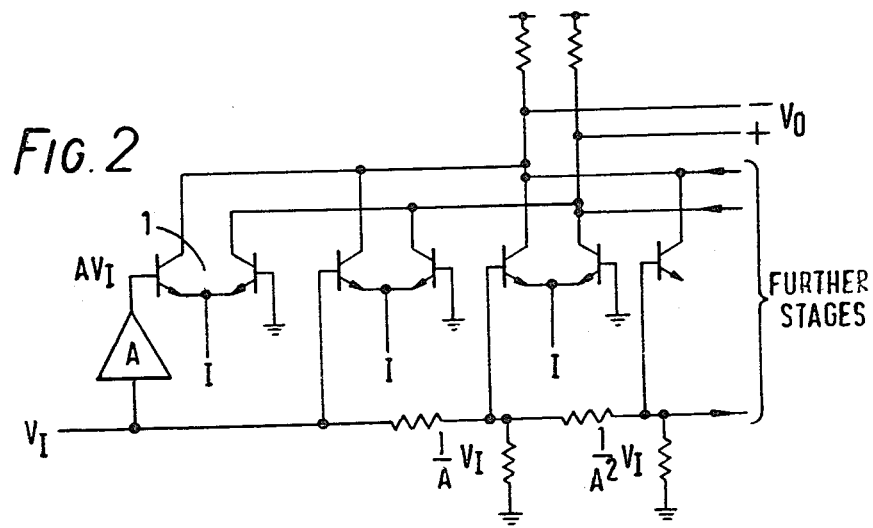
FIG. 2 shows a logarithmic amplifier suitable for the invention.

To provide such an amplifier accurate to less than 1 dB for a typical range of input of 80 dB or more the arrangement of FIG. 2 is used. A series of identical long tailed pairs, such as 1 is fed successively with input signals $V_I$ amplified or attenuated, as shown, in successive stages by A, 1, 1A, $1/A^2$, etc. The long tailed pairs feed a common load.

Figure 1:
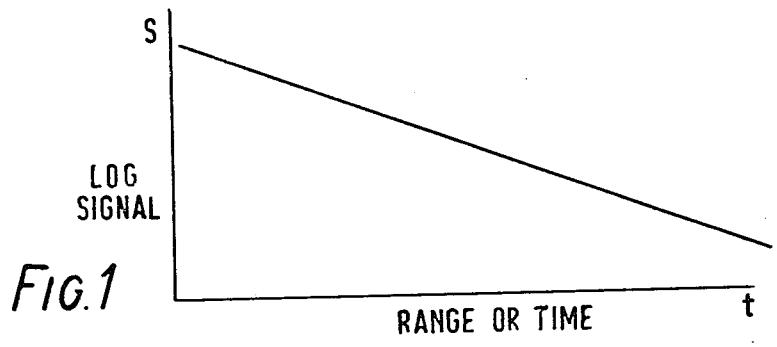
Figure 3:
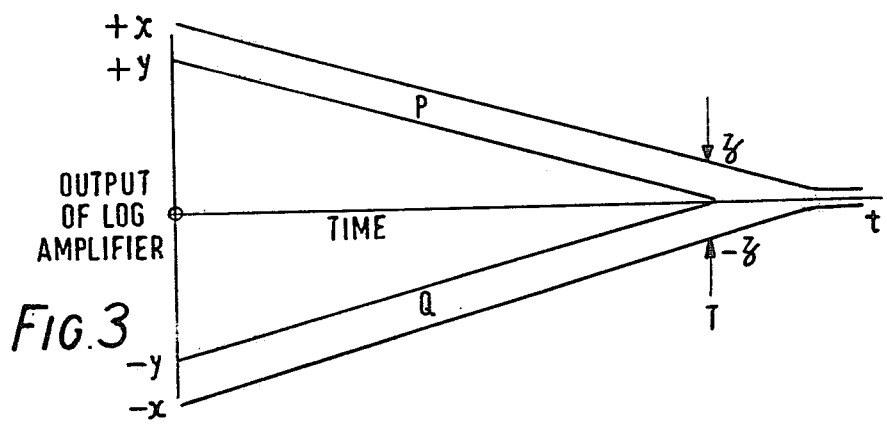
FIG. 3 shows the envelope of an output signal from such an amplifier.

FIG. 3 shows the envelope of the output signal from such an amplifier, when fed with a typical reflected signal as shown in FIG. 1, falling linearly with time from an amplitude $\pm \chi$ at time zero to $\pm z$ at T, finally departing from linearity and becoming asymptotic to the axis as the amplifier reaches the end of its logarithmic range.

it is assumed that a certain dynamic range of signal in dB is acceptable, and that this range corresponds to the peak amplitude of $\pm z$. It can be seen that if a signal, corresponding to the triangle of amplitude y at time zero (where $x - y = z$) and zero at time T and thus representing log L, is subtracted from the output of the amplifier then the remaining signal (areas P & Q) represents a constant output envelope with time, of amplitude z and compressed by a logarithmic law, thus providing log E. The value of y represents the overall gain range of the circuit and may typically be 60 dB. This gain range may be varied as desired but the amplifier should not be used for signal levels which take it out of its logarithmic range.

Figure 4:
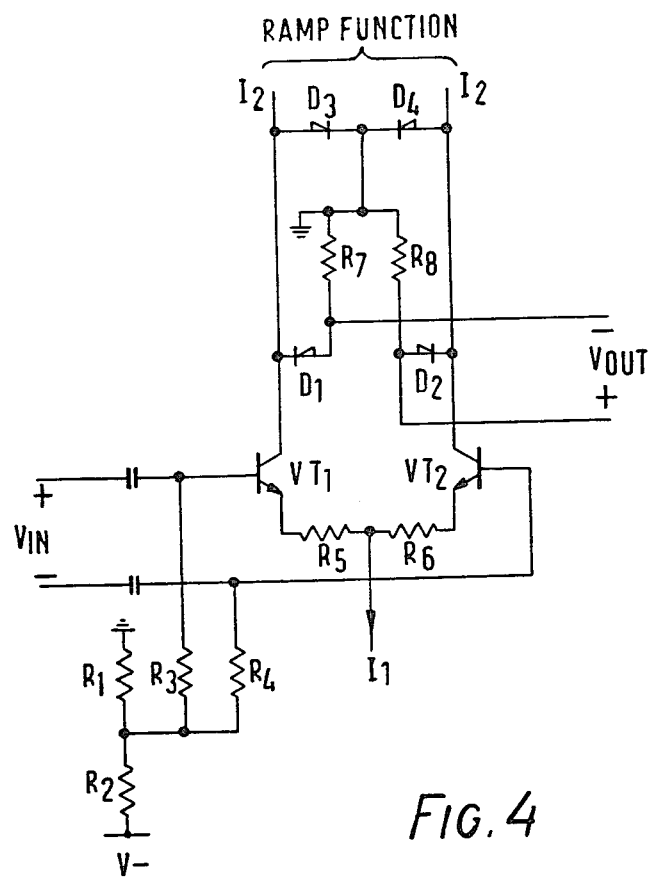
FIG. 4 shows in simplified form a circuit for the invention.

A circuit shown in simplified form in FIG. 4 accomplishes the subtraction. A long tailed pair $VT_1$, $VT_2$ is fed with a constant emitter current $I_1$. The collectors are fed from two equal variable current sources feeding currents $I_2$. Input derived from the logarithmic amplifier of FIG. 2 is capacitively coupled to the bases of $VT_1$ & $VT_2$, which is biased via resistors $R_3$ and $R_4$ to a negative potential set up by a divider $R_1$, $R_2$. The ramp current $I_2$ is greater than $I_1/2$ at time zero and is arranged to fall linearly to exactly $I_1/2$ at time T when the ramp terminates. For zero differential input the current $I_1$ divides equally between $VT_1$ and $VT_2$, and since $I_2 > (I_1/2)$ both collectors rise positively, their excursion being limited by diodes $D_3$ and $D_4$.

Figure 5:
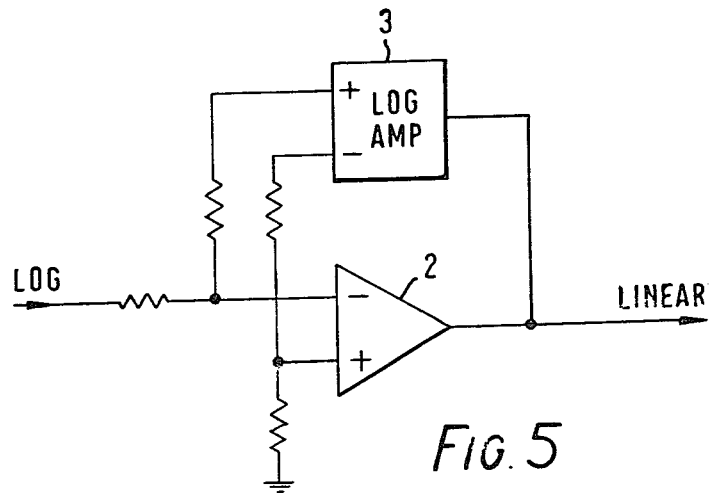
FIG. 5 shows an antilogarithmic circuit.

As soon as a differential input voltage Vin is applied this balance is disturbed and the two currents ($I_1/2$) are respectively augmented and diminished by a current $V_{in}/(R_5 + R_6)$ (it is assumed that resistors $R_5$ and $R_6$ are equal and much greater than $(25/I_1) \times 2$ the emitter impedance of $VT_1$ and $VT_2$). When on one side or other of the pair, depending on the input polarity, the collector current $(I_1/2) + [V_{in}/(R_5 + R_6)]$ becomes greater than $I_2$ then that collector falls and either of the two diodes $D_1$ or $D_2$ is put into conduction, diodes $D_3$ or $D_4$ then being reverse biased. The current through diodes $D_1$ or $D_2$, $(I_1/2) + [V_{in}/(R_5 + R_6)] - I_2$, develops an output voltage across resistors $R_7$ or $R_8$, the other collector remaining unaffected and giving zero output. This accomplishes the desired function of producing an output only when the input, in either polarity, exceeds a threshold which is variable with time. This gives the effect of subtracting the logarithm of the loss function from that of the signal. The two regions, of FIG. 3, which are required to produce output, viz P & Q, then do so separately at each collector. The signals from the collectors may then be combined conventionally in antiphase to produce a push pull signal, or if summed in phase produce as output the required full wave rectified and compressed signal. It is desirable, in order to remove distortion components caused by the switching action of the diodes as the signal goes from P to Q and vice versa, that the output signal be low pass filtered. Should a linear output be required then an antilog circuit such as that of FIG. 5 may be utilized. Such a circuit comprises an operational amplifier 2 with a 'logarthmic' amplifier 3, such as that described, in the feedback path.

The circuits shown produce the equivalent of a swept gain function to a high degree of accuracy limited by the precision of the 'logarithmic' amplifier and the linearity of the ramp signal. If some other gain function is desired then a non linear ramp signal can be readily substituted. The circuit produces a compressed output and can be summed so as to produce either an effectively rectified output, or a full wave signal. A linear output may be simply derived.

Figure 6:
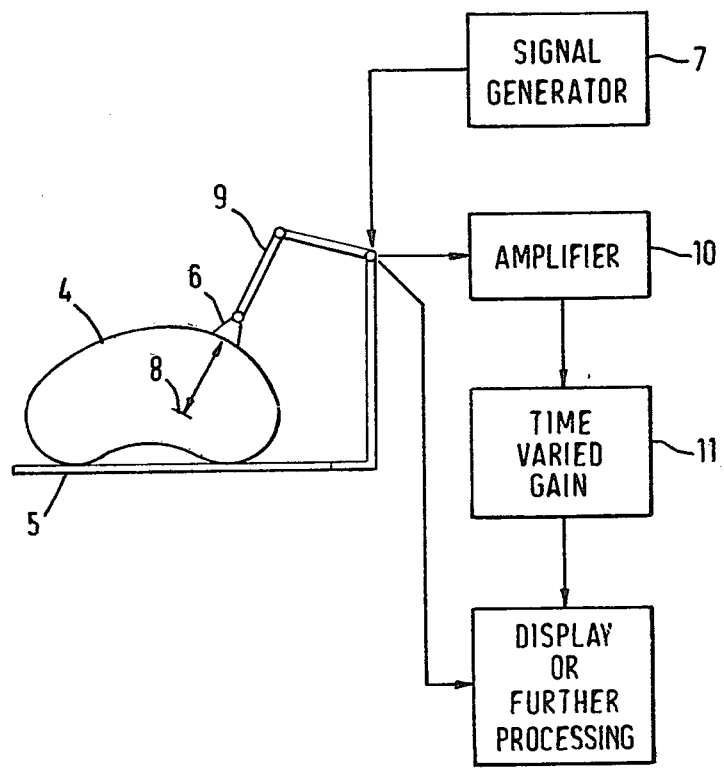
FIG. 6 illustrates the manner in which the processing arrangement of the invention is used with a known type of ultrasonic investigative apparatus.

The circuits described herein for providing time varied gain can be used with, and assist efficient operation of ultrasonic investigative systems such as that shown in simplified form in FIG. 6.

A body 4 which may be a living body, is placed on a surface 5 and insonified by a receiving transducer which, in this example is also the transducer 6. A mechanical arm 9 holds the transducer 6 and provides positional control and information relative to surface 5 and hence the body 4.

The received signals are amplified at an amplifier 10 and then subject to time varied gain in circuits 11 which are beneficially as described hereinbefore. Of course amplifier 10 may, in practice, be combined with circuits 11.

The resultant signals, in logarithmic form or otherwise, are then output to a display or known types of further processing at 12. The operations at 12 may be coordinated by the positional information from arm 9.

What I claim is:

1. An arrangement for processing signals, representing received pulses of energy which have been subject to attenuation which is a function of their propagation time, including means for converting the signals to logarithmic form, means for generating a further signal, representing the logarithm of the attenuation function and means for effectively subtracting the further signal from the logarithmically converted first mentioned signals, to make the signals more representative of said pulses in the absence of attenuation.

2. An arrangement according to claim 1 in which the means for subtracting is arranged to pass only signals whose positive or negative going excursions exceed a threshold representative of said further signal.

3. An arrangement according to claim 1 including means for providing the antilogarithm of the signals after said subtraction.

4. An arrangement according to claim 1 in which the attenuation function is an exponential function and said further signal is a linear ramp signal.

5. A system for investigating a region of interest by means of reflected energy including means for transmitting pulses of energy, means for receiving the pulses, after reflection at an object or other reflective feature and after suffering attenuation which is a function of their propagation time, and for providing signals representative of said received pulses and processing means including means for converting the signals to logarithmic form, means for generating a further signal, representing the logarithm of the attenuation function, and means for effectively subtracting the further signal from the logarithmically converted first mentioned signals, to make the signals more representative of said pulses in the absence of attenuation.

6. A system for investigating a region of interest by means of ultrasonic energy including means for transmitting pulses of ultrasonic energy into a medium in which the region of interest is located, means for receiving the pulses after reflection at a reflective feature in the region of interest and after suffering attenuation in the medium according to an attenuation function, which is an exponential function of their propagation time, and for providing signals representative of said received pulses and processing means including means for converting the signals to logarithmic form, means for generating a linear ramp signal, representing the logarithm of the attenuation function, and means for effectively subtracting the ramp signal from the logarithmically converted first mentioned signals to counter the effects of attenuation in said medium.

* * * * *

UNITED STATES PATENT AND TRADEMARK OFFICE
CERTIFICATE OF CORRECTION

PATENT NO. : 4,145,741
DATED : March 20, 1979
INVENTOR(S) : Donald NAPPIN

It is certified that error appears in the above-identified patent and that said Letters Patent are hereby corrected as shown below:

In Section 73, add "Assignee: EMI Limited, Hayes, Middlesex, England

Signed and Sealed this

Twenty-first Day of August 1979

[SEAL]

Attest:

Attesting Officer

LUTRELLE F. PARKER
Acting Commissioner of Patents and Trademarks